| United States Patent [19] | [11] | Patent Number: | 4,906,390 |
|---|---|---|---|
| Horodysky | [45] | Date of Patent: | Mar. 6, 1990 |

[54] BORATED DIOL-PHENOL SULFIDE PRODUCT AND LUBRICANT COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 59,245

[22] Filed: Jun. 8, 1987

Related U.S. Application Data

[63] Continuation of Ser. No. 898,888, Aug. 21, 1986, abandoned, which is a continuation of Ser. No. 634,860, Jul. 26, 1984, abandoned.

[51] Int. Cl.$^4$ ................ C10M 135/00; C10M 139/00
[52] U.S. Cl. ............................. 252/46.3; 252/32.7 R; 252/17; 252/34; 252/46.6; 558/287
[58] Field of Search ................ 252/46.3, 46.6, 49.6, 252/32.7 R, 17, 34; 260/462 R; 558/287

[56] References Cited

U.S. PATENT DOCUMENTS

| 2,795,548 | 6/1957 | Thomas et al. | 252/49.6 |
|---|---|---|---|
| 2,975,135 | 3/1961 | Darling et al. | 252/49.6 |
| 2,979,459 | 4/1961 | Darling et al. | 252/49.6 |
| 3,224,971 | 12/1965 | Knowles et al. | 260/462 R |
| 3,646,098 | 2/1972 | Cyba | 260/462 R |
| 4,305,832 | 12/1981 | Braid | 252/48.2 |
| 4,394,276 | 7/1983 | Small, Jr. | 252/32.7 E |
| 4,394,277 | 7/1983 | Small, Jr. | 252/49.6 |
| 4,472,289 | 9/1984 | Horodysky et al. | 252/49.6 |

*Primary Examiner*—Jacqueline V. Howard
*Assistant Examiner*—Margaret B. Medley
*Attorney, Agent, or Firm*—Alexander J. McKillop; Michael G. Gilman; Charles J. Speciale

[57] ABSTRACT

Reduction of friction between metal parts in contact, reductions in corrosion of copper and oxidation of lubricants are made possible by adding to lubricant or liquid fuel a minor amount of a product made by reacting a hydrocarbyl diol, a phenol sulfide and a boron compound.

27 Claims, No Drawings

BORATED DIOL-PHENOL SULFIDE PRODUCT AND LUBRICANT COMPOSITIONS CONTAINING SAME

This is a continuation of copending application Ser. No. 898,888, filed on Aug. 21, 1986, which is a continuation of application Ser. No. 634,860 filed Jul. 26, 1986, now both abandoned.

BACKGROUND OF THE INVENTION

1. Field of the Invention

The invention is concerned with certain additives and with lubricant and fuel compositions containing them. It more particularly relates to a hydrocarbon diol phenol sulfide borate and to lubricant and fuel compositions containing same.

2. Discussion of the Prior Art

It is known to us borated compounds in lubricants and fuels. These include borated alkanolamines, such as those disclosed in U.S. Pat. No. 4,382,006, and certain borated sulfur compounds, such as are exemplified in U.S. Pat. No. 4,394,277. Other U.S. Pat. Nos. disclosing additional borated additives are: 2,994,064; 3,007,873; 3,014,869; 3,014,869; 3,014,870; 3,076,835; 3,254,025; 3,449,362; 4,025,445; 4,328,113; 4,376,712; and 4,426,723.

The use of certain phenol sulfides in lubricants is known also. U.S. Pat. No. 4,305,832 discloses phenol sulfides, disulfides, polysulfides and oligomers thereof with alkyl ring ethers for the purpose. U.S. Pat. No. 4,330,421 discloses lubricants containing calcium phenol sulfides.

The additives and the lubricant and fuel compositions described herein provide sustantial high temperature stability, friction reduction and antioxidant and antiwear properties. Such additives per se, and the compositions made therewith are new and have not, to the best of our knowledge, been described or suggested in the prior art in lubricants.

SUMMARY OF THE INVENTION

The invention provides (1) a product of reaction made by reacting a hydrocarbyl diol, a phenol sulfide and a boron compound (2) a lubricant or fuel composition containing same and (3) a method of reducing fuel consumption in an internal combustion engine with such composition.

BACKGROUND OF THE INVENTION

The hydrocarbon diols useful in the practice of this invention have the formula

R(OH)$_2$ wherein R is a hydrocarbyl group containing 8 to 30 carbon atoms, preferably 12 to 18 carbon atoms, including mixtures thereof. The two hydroxy groups may be on any two carbon atoms along the chain, but they are preferably near the end of the hydrocarbyl chain and are preferably vicinal. The hydrocarbyl groups are preferably alkyl groups, but may also be aryl, alkaryl, aralkyl, alkenyl, cycloalkyl and cycloalkenyl groups. The aliphatic groups, including the alkyl portions of the aryl members, may be linear or branched, saturated or unsaturated.

Among the diols contemplated are 1,2-octanediol, 1,2-decanediol, 1,2-dodecanediol, 1,2-tetradecanediol, 1,2-pentadecanediol, 1,2-hexadecanediol, 1,2-heptadecanediol, 1,2-octadecanediol, 1,2-eicosanediol, 1,2-triacontanediol, mixed 1,2-C$_{15}$ to C$_{18}$ alkanediols, diols derived from the epoxidation of propylene oligomers, such as the propylene tetramer, and butylene oligomers, such as the butylene trimer, and mixtures of any of these diols. Mixtures are often preferred.

The vicinal diols can be synthesized using several methods known to the art. One such method, described in an article in *J. Am. Chem. Soc.*, 68, 1504 (1946), involves the hydroxylation of 1-olefins with peracids. Vicinal diols can also be prepared by the peroxytrifluoroacetic acid method for the hydroxylation of olefins as described in *J. Am. Chem. Soc.*, 76, 3472 (1954). Similar procedures can be found in U.S. Pat. Nos. 2,411,762, 2,457,329 and 2,455,892. These are incorporated herein by reference.

The diols can also be prepared via catalytic epoxidation of an appropriate olefin, followed by hydrolysis.

As disclosed hereinabove, the preferred diols are vicinal diols containing 12 to 18 carbon atoms. This range is preferred because diols having much less than 12 carbon atoms have significantly less friction reducing properties, while in those having more than 20 carbon atoms, solubility constraints or other adverse physical effects become significant. More preferred are the C$_{14}$ to C$_{18}$ hydrocarbyl groups and mixtures of such hydrocarbyl groups in which solubility, frictional characteristics and other properties appear to be maximized.

Sulfurized phenols useful for the purpose of this invention have the formula

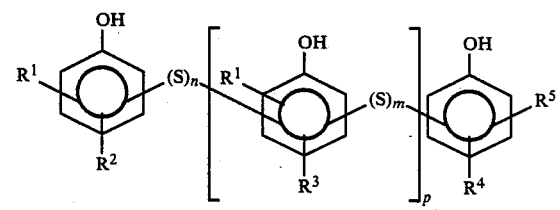

wherein R$^1$, R$^2$, R$^3$, R$^4$ and R$^5$ are hydrogen or the same or different hydrocarbyl groups containing 1 to 20 carbon atoms in any isomeric structural arrangement, and wherein with respect to R$^2$, R$^3$ and R$^4$ the total number of carbon atoms represented thereby cannot be less than 4 if 1 or 2 of such members are hydrogen, n and m are 1 to 4 and may be the same or different and p is 0 to 4. The sulfide, disulfide or polysulfide bridges may be at any of the ring positions, but positions ortho or para to the hydroxy groups are preferred, with ortho positions being more preferable. The hydrocarbyl group is preferably an alkyl group, including methyl, butyl, octyl, dodecyl, tetradecyl and octadecyl or an aryl, aralkyl, alkaryl, alkenyl, cycloalkyl or cycloalkenyl group. "Aryl" will contain 6 to 14 carbon atoms in the ring.

In general, sulfurized phenols can be made by any method known to the art. In one method the phenol (e.g., p-t-octylphenol) is initially reacted with a sulfur halide (e.g., sulfur monochloride or dichloride) in a 1:1 to 3:1 ratio with a 3:2 ratio often preferred, and the resulting phenol sulfide may, if desired, be further reacted with other phenols and sulfur halide. Preferred phenol reactants include hydrocarbyl-substituted phenols.

The novel compounds disclosed herein may be prepared from any suitable phenol sulfide, disulfide, polysulfide or oligomer thereof. Preferred are 2,2'-thiobis- (alkylphenols), i.e., n=1 and p=0, or 2,2'-dithiobis(alkylphenols), i.e., n=2 and p=0, and oligomeric 2,2'-thiobis(alkylphenols). Preferred also are the thiobis(alkylphenols) containing 3 or 4 alkylphenol units, particularly those containing both sulfide and disulfide groups. In this latter case, when there are 3 alkylphenol units, p is 1 and n and m are at least 1. When there are 4 alkylphenol units, p is 2 and n and m are at least 1. More preferred are alkyl moieties containing from 4 to 12 carbon atoms. Especially preferred are groups such as nonyl and dodecyl or mixtures thereof, often derived from propylene trimers, propylene tetramers or mixtures thereof, respectively, substituted in the para position with respect to the hydroxyl group of the phenol.

Boration may be with any boron compound capable of reacting. Preferred are the metaborates, boric acid, boric oxide and alkyl borates of the formula

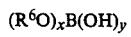

$$(R^6O)_xB(OH)_y$$

wherein $R^6$ is a $C_1$ to $C_6$ alkyl group, x is 1 to 3 and y is 0 to 2, the sum of x and y being 3. The alkyl borates contemplated are the mono-, di- and trialkyl borates, i.e., the mono-, di- and trimethyl borates, mono-, di- and triethyl borates, mono-, di- and tripropyl borates, mono-, di- and tributyl borates, mono-, di- and triamyl borates and mono-, di- and trihexyl borates.

The products of the invention may be made by mixing all three reactants together and heating for the required time. It is contemplated that the reaction can be carried out at from about 80° C. to about 260° C., depending upon the reactants and whether or not a solvent is used. The reaction mixture will probably have therein at least a stoichiometric amount of boron compound based on available reactive hydroxyl and hydroxy linkages. Excess boron can be used, so that the final product will have from about 0.01% to about 10% of boron per se therein. This amount of boron includes an amount which "overborates" the product. Thus, for certain applications it obviously is advantageous to use excess borating compound, including a 50 to 100% excess. Overall, the molar ratios of phenol:diol:boron compound may range from about 1:1:1 to about 1:6:8, preferably from about 1:2:1 to about 1:4:4 to form the mixed borate.

While atmospheric pressure is generally preferred, this reaction, or the ones mentioned below, can be advantageously run at from about 1 to about 5 atmospheres. Furthermore, where conditions warrant it, a solvent may be used and is often preferred. In general, any relatively non-polar, unreactive solvent can be used, including benzene, toluene, xylene and 1,4-dioxane. Other hydrocarbon and alcoholic solvents, the latter of which include propanol, butanol and the like, can be used but is not generally preferred. Mixtures of alcohol and hydrocarbon solvents can be used also.

It is not believed that the time of reaction is critical and that any of the reactions mentioned herein can be carried out in from about 1 to about 20 hours.

While it is preferred to prepare the product by mixing all reactants initially, it will be understood by the art that variations that give substantially similar products with substantially the same activity are deemed to be within the invention.

Examples of variations that we believe will substantially produce the product of our invention are:
 (1) (boron compound+diol)+phenol sulfide;
 (2) (boron compound+phenol sulfide)+diol in which the reactants in the parentheses are reacted first and the product obtained is reacted with the third reactant.

The liquid fuels improved in accordance with the present invention comprise those which are normally susceptible to forming undersirable carburetor and intake valve deposits in internal combustion engines. Specifically, liquid hydrocarbon fuels boiling from about 75° F. to about 750° F., including gasoline, jet fuel and dies fuel may be mentioned. Of particular significance is the treatment of petroleum distillate fuels having an initial boiling point of about 75° F. to about 135° F. and an end boiling point from about 250° F. to about 750° F. It should be noted, in this respect, that the term "distillate fuels" or "distillate fuel oils" is not intended to be restricted to straight-run distillate fractions. These distillate fuel oils can comprise straight run distillate fuel oils, catalytically or thermally cracked (including hydrocracked) distillate fuel oils or mixtures of straight run distillate fuel oils, naphthas and the like, with cracked distillate stocks. Moreover, such fuel oils can be treated in accordance with such well known commercial methods as acid or caustic treatment, hydrogenation, solvent refining, clay treatment and the like.

The distillate fuels are characterized by their relatively low viscosity, pour point and the like. The principle property which characterizes these hydrocarbons, however, is their distillate range. As hereinbefore indicated, this range will lie between about 75° F. and about 750° F. Obviously the distillation range of each individual fuel will cover a narrower boiling range, falling nevertheless, within the above-specified limits. Likewise, each fuel will boil substantially continuously throughout its distillation range.

In addition to the hydrocarbon fuels mentioned, other fuels improved by the disclosed additives are alcohols such as methyl alcohol and ethyl alcohol, mixtures thereof and mixtures with the hydrocarbon fuels disclosed herein.

Particularly contemplated among the fuels or fuel oils are Nos. 1, 2 and 3 fuel oils, used in heating and as diesel fuel oils, gasoline and jet combustion fuels. The domestic fuel oils generally conform to the specifications set forth in ASTM specification D396-48T. Specifications for diesel fuels are defined in ASTM specification D975-48T. Typical jet fuels are defined in military specification MIL-F-624B. In addition, fuel oils of varying viscosity and pour points falling both within and outside the indicated ranges may also be effectively treated through the use of the additives of the present invention.

In general, the disclosed additives are employed in the liquid fuel in a minor amount, i.e., an amount effective for imparting the desired activity. More specifically, it can be used at a concentration from about 0.001 to about 10 wt % and preferably from about 0.01 to 0.5 wt. % based on the total weight of the fuel. The concentration of the additive of this invention in fuels may also be stated in terms of pounds of fuel per 1000 barrels thereof. Thus, the additives can be used in the fuel within the range of from about 25 pounds/1,000 barrels to about 500 pounds/1,000 barrels. Any other known additive (as for example, antioxidants and dispersants) generally, may also be used in fuel compositions containing the additives hereof for their known purposes without adverse effect to such compositions.

The disclosed products may also be incorporated in lubricating medium which may comprise either a mineral oil, a synthetic oil or mixtures thereof, or a grease in which any of the aforementioned oils are employed as a vehicle. The resulting composition can also contain detergents and dispersants, as well as antioxidants, inhibitors, antiwear, extreme pressure, antifoam, pour depressant and viscosity index improving additives without negating the beneficial properties of the novel compositions of this invention. The compositions can include commonly used additives such as phenates, sulfonates, polymers, metal dithiophosphates such as zinc or molybdenum dithiophosphates, succinimides, and the like.

In general, mineral oils employed as the lubricant or gease vehicle may be of any suitable lubricating viscosity range as, for example, from about 45 SSU at 100° F. to about 6,000 SSU at 100° F., and preferably from about 50 SSU at 210° F. to about 250 SSU at 210° F. These oils may have viscosity indexes varying from below 0 to about 100 or higher. Viscosity indexes from about 70 to about 95 are perferred. The average molecular weights of these oils may range from about 250 to 800. Where the lubricant is to be employed in the form of a grease, the lubricating oil is generally employed in an amoung sufficient to balance the total grease composition, after accounting for the desired quantity of the thickening agent, and other additive components to be included in the grease formulation.

Synthetic oils and mixtures of synthetic oil and mineral oil may be successfully utilized in this invention. Typical synthetic oils include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, di(-butylphthalate) fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diophenyl ethers typified by a butyl-substituted bis(p-penoxyl phenyl) ether, phenoxy phenylethers, etc.

A wide variety of thickening agents can be used in forming the greases of this invention. Included among the preferred thickening agents are alkali and alkaline earth metal soaps of fatty acids and fatty materials having from 12 to about 30 carbon atoms per molecule. The metals are typified by sodium, lithium, calcium and barium. Fatty materials are illustrated by stearic acid, hydroxy-stearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyamines, indanthrene, pigments such as perylimides, pyromellitdiimides, and ammeline.

The preferred thickening agents employed in the grease compositions are essentially hydrophobic clays. Such thickening agents can be prepared from clays which are initially hydrophlilic in character, but which have been converted into a hydrophobic condition by the introduction of long-chain hydrocarbon radicals onto the surface of the clay particles; prior to their use as a component of a grease composition, as, for example, by subjecting them to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention.

The following Examples provide specific illustrations of the products and compositions of the invention. They are illustrative only, and are not meant to limit the invention.

EXAMPLE 1

Mixed Borate of 1,2Mixed Pentadecanedioloctadecanediol and Dodecylphenol Sulfide Approximately 120 g of 1,2-mixed pentadecanedioloctadecanediol containing approximately 28% 1,2-pentadecanediol, 28% 1,2-hecadecanediol, 28% 1,2-hepetadecanediol and 16% 1,2-octadecanediol, 138 g of 50% dodecylphenol sulfide (made by reacting 3 moles of dodecylphenol with 2 moles of sulfur dichloride at 100° C. to 150° C. for six hours with agitation followed by vacuum topping to remove residual HCl ), in 100" solvent paraffinic neutral lubricating diluent oil, 100 g of toluene solvent and 28.5 g boric acid were charged to a reactor equipped with agitator, heater, Dean-Stark tube with condenser and provision for maintaining an inert nitrogen atompshere. The reactor contents were heated up to 180° C. over a period of eight hours until water evolution as a result of azeotropic distillation ceased. A total of 22 g of water was collected. The solvent was removed by distillation at 175° C. under reduced pressure. The product was then diluted with an additional 130 g of 100" solvent paraffinic neutral lubricating oil to further improve the handling and subsequent blending of the product of this example. The product was filtered through diatomaceous earth. The finished concentrate contained 1.2% boron, 77% carbon and 11.9% hydrogen.

EXAMPLE 2

Mixed Borate of 1,2-Mixed Pentadecanedioloctadecanediol and Dodecylphenol Sulfide Approxiately 81 g of 1,2-mixed pentadecanedioloctadecanediol, 150 g of dodecylphenol sulfide-oil concentrates (both described in Example 1), 100 g of toluene and 17 g of boric acid were charged to a reactor equipped as generally described in Example 1. The reactor contents were heated up to 170° C. over a period of 7 hours until water evolution ceased. A total of 13 g of water was collected. The solvent was removed by vacuum topping at 170° C. and the product was filtered at 120° C. through diatomaceous earth.

EXAMPLE 3

Mixed Borate of 1,2-Mixed Pentadecanedioloctadecanediol and Dodecylphenol Sulfide Approximately 81 g of 1,2-mixed pentadecanedioloctadecanediol (as described in Example 2), 150 g of dodecylphenol sulfide oil concentrate (as described in Example 1), 100 g of toluene and 34 g of boric acid were charged to a reactor equipped as generally described in Example 1. The reactor contents were heated up to 170° C. over a period of eight hours until water evolution ceased. A total of 19 g of water was collected. The solvent was removed by vacuum topping at 170° C. and the product was filtered through diatomaceous earth.

EXAMPLE 4

1,2-Hexadecanediol-Dodecylphenol Sulfide Borate

Approximately 80 g of 1,2-hexadecanediol, 150 g of the dodecylphenol sulfide concentrate described in Example 1, 150 g of toluene and 17 g of boric acid were charged to a reactor equipped as generally described in Example 1. The reactor contents were heated up to 170° C. over a period of six hours until water evolution during azeotropic distillation ceased. The solvent was removed by distillation under reduced pressure, and the product was filtered through diatomaceous earth.

EXAMPLE 5

1,2-Hexadecanediol-Dodecylphenol Sulfide Borate

Approximately 81 g of 1,2-hexadecanediol, 150 g of the dodecylphenol sulfide concentrate described in Example 1, 150 g of toluene and 34 g of boric acid were charged to a reactor equipped as generally described in Example 1. The reactor contents were heated up to 170° C. over a period of ten hours until water evolution ceased. The solvent was removed by distillation under reduced pressure and the product was filtered through diatomaceous earth.

EVALUATION OF THE COMPOUNDS

The products were evaluated in a Low Velocity Friction Apparatus (LVFA) in a fully formulated 5W-30 synthetic or a fully formulated 10W-40 mineral automotive engine oil containing an additive package which includes antioxidant, dispersant and detergent. They were also tested as antioxidants and for their ability to reduce copper corrosion. The test compounds were used at concentrations by weight of the total weight of oil shown in the tables. They also summarize the test results obtained in the various tests.

Description

The Low Velocity Friction Apparatus (LVFA) is used to measure the coefficient of friction of test lubricants under various loads, temperatures, and sliding speeds. The LVFA consists of a flat SAE 1020 steel surface (diameter 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricants are placed on the LVFA. A 240 psi load is applied, and the sliding speed is maintained at 40 fpm at ambient temperature for a few minutes. A plot of coefficients of friction ($U_k$) vs. speed were taken at 240, 300, 400, and 500 psi. Freshly polished steel specimens are used for each run. The surface of the steel is parallel ground to 4 to 8 microinches. The results in Tables 1 and 2 refer to percent reduction in friction compared to the unmodified oil. That is, the formulation mentioned above was tested without the compound of this invention and this became the basis for comparison. The results were obtained at 250° F. and 500 psi.

TABLE 1

Evaluation of Friction Reducing Characteristics Using Low Velocity Friction Apparatus

| Composition | Additive Conc. in Test Oil wt. % | % Reduction of Coefficient of Friction | |
|---|---|---|---|
| | | 5 ft/Min | 30 Ft/Min |
| Test Oil(SAE 5W-30 fully formulated synthetic automotive engine oil with detergent/dispersant/inhibitor package | — | 0 | 0 |
| Example 1 Plus Test Oil | 4 | 44 | 36 |
| | 2 | 39 | 33 |
| | 1 | 37 | 31 |
| | 0.5 | 31 | 27 |
| Example 2 Plus Test Oil | 4 | 41 | 35 |
| Example 3 Plus Test Oil | 4 | 31 | 30 |
| Example 4 Plus Test Oil | 4 | 40 | 31 |
| Example 5 Plus Test Oil | 4 | 48 | 35 |

TABLE 2

Evaluation of Friction Reducing Characteristics Using Low Velocity Friction Apparatus

| Composition | Additive Conc. in Test Oil wt. % | % Reduction of Coefficient of Friction | |
|---|---|---|---|
| | | 5 ft/Min | 30 Ft/Min |
| Test Oil(SAE 10W-40 fully formulated mineral automotive engine oil with detergent/dispersant/inhibitor package | — | 0 | 0 |
| Example 3 Plus Test Oil | 4 | 33 | 29 |
| Example 4 Plus Test Oil | 4 | 35 | 21 |
| Example 5 Plus Test Oil | 4 | 42 | 32 |

The products were also evaluated for high temperature and oxidative stability. In most cases, improvements in oxidative stability were observed. Basically, the test lubricant was subjected to a stream of air bubbled through it at a rate of 5 liter per hour at 325° F. for forty hours. Present in the composition were samples of metals commonly used in engine construction, namely iron, copper, aluminum and lead. See U.S. Pat. No. 3,682,980 for further details of the test. Improvements in percent viscosity increase, control of acidity and/or control of lead loss show effective control.

TABLE 3

| | CATALYTIC OXIDATION TEST | | | |
|---|---|---|---|---|
| | Conc., Wt. % | % Increase in Viscosity of Used Oil vs. New Oil @ 100° C., KV | Acid No. | Pb Loss, Mg |
| Test Oil 200" Solvent Paraffinic Neutral Mineral Lubricating Oil | — | 27 | 2.21 | 0.4 |
| Example 1 plus Test Oil | 2 | 22 | 2.25 | 0.1 |
| | 1 | 16 | 1.38 | 0.2 |
| Example 2 plus Test Oil | 1 | 17 | | |
| Example 3 plus Test Oil | 1 | 8 | | |
| Example 4 plus Test Oil | 1 | 10 | | |
| Example 5 plus Test Oil | 1 | 14 | | |

The product's propensity to corrode copper (due primarily to the contained sulfur groups) was measured in lubricants using the ASTM D-130-80 Copper Strip Corrosivity Test at two different, very severe, conditions of time and temperature. As can be seen from the data, the products of the examples are surprisingly non-corrosive to copper

TABLE 4

| | COPPER STRIP CORROSIVITY | | |
|---|---|---|---|
| Product in Oil | Conc. in 200" SPN Test Oil Wt. % | ASTM D130-80 3 Hrs. @ 250° F. | ASTM D130-80 6 Hrs. @ 212° F. |
| Example 1 | 3 | 1A | 1B |
| Example 2 | 1 | 1A | 1A |
| Example 3 | 1 | 1A | 1A |
| Example 4 | | | |

The products of this invention have been discussed as reaction products. This is because the reaction system is a complex one which produces a product difficult to describe as a distinct compound. However, I nonetheless believe that when equivalent amounts of a vicinal diol with a terminal OH group, a sulfurized phenol and a boron compound such as boric acid are reacted, the product comprises some or even a predominant amount of compound of the formula:

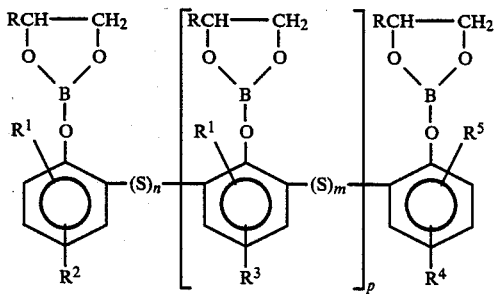

wherein R, $R^1$, $R^2$, $R^3$, $R^4$, $R^5$, m, n and p are as defined hereinabove. More specifically, when 1,2-hexadecanediol, dodecylphenol and boric acid are reacted, the product will comprise a compound wherein in this formula R is a tetradecyl group, $R^2$, $R^3$ and $R^4$ are dodecyl groups and $R^1$ and $R^5$ are hydrogen.

What is claimed is:

1. A product of the reaction made by reacting a hydrocarbyl diol of the formula $R(OH)_2$ wherein R is a hydrocarbyl group containing from 8 to 30 carbon atoms, with a phenol sulfide of the formula

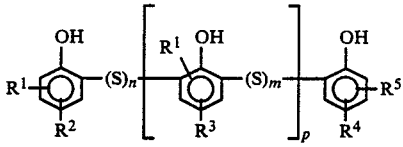

wherein $R^1$, $R^2$, $R^3$, $R^4$ and $R^5$ are hydrogen or the same or different hydrocarbyl groups containing from 1 to 20 carbon atoms, m and n are 1 to 4 and p is 0 to 4 with a boron compound capable of reacting with said hydrocarbyl diol and selected from the group consisting of metaborates, boric acid, and alkylborates of the formula $(R^6O)_xB(OH)_y$ wherein $R^6$ is a $C_1$ to $C_6$ alkyl group, x is 1 to 3 and y is 0 to 2, the sum of x and y being 3, the mole ratio of phenol to diol to boron compound ranging from about 1:1:1 to about 1:6:8, respectively, and at a pressure of about 1 to about 5 atmospheres and a temperature of about 80° C. to about 260° C.

2. The product of claim 1 wherein R is alkyl, aryl, alkaryl, aralkyl, alkenyl, cycloalkyl or cycloalkenyl.

3. The product of claim 1 wherein the diol is selected from the group consisting of 1,2-octanediol, 1,2-decanediol, 1,2-dodecanediol, 1,2-tetradecanediol, 1,2-pentadecanediol, 1,2-hexadecanediol, 1,2-heptadecanediol, 1,2-eicosanediol, 1,2-triacontanediol, mixed $C_{15}$ to $C_{18}$ alkanediols, diols derived from the epoxidation of propylene, diols derived from the epoxidation of butylene and mixtures of any of these.

4. The product of claim 1 wherein $R^1$, $R^2$, $R^3$, $R^4$ and $R^5$ are hydrogen, alkyl, aryl, aralkyl, alkaryl, alkenyl, cycloalkyl or cycloalkenyl groups.

5. The product of claim 4 wherein the phenol sulfide is a 2,2'-thiobis(alkylphenol) wherein n=2 and p=0, 2,2'-dithiopbis(alkylphenol) wherein n=2 and p=0 and thiobis(alkylphenol) wherein p=1 or 2.

6. The product of claim 1 wherein the boron compound is boric acid.

7. The product of claim 1 wherein the alkyl borate is a mono-, di- or trialkyl borate, the alkyl portion being a methyl, ethyl, propyl, butyl, amyl or hexyl group.

8. The product of claim 1 wherein the diol is a mixture of $C_{15}$ to $C_{18}$ alkanediols, the phenol sulfide is dodecylphenol sulfide and the boron compound is boric acid.

9. The product of claim 1 wherein the diol is 1,2-hexadecanediol, the phenol sulfide is dodecylphenol sulfide and the boron compound is boric acid.

10. A lubricant composition comprising lubricant and a friction reducing amount of product of reaction made by reacting a hydrocarbyl diol of the formula $R(OH)_2$ wherein R is a hydrocarbyl group containing from 8 to 30 carbon atoms, with a phenol sulfide of the formula

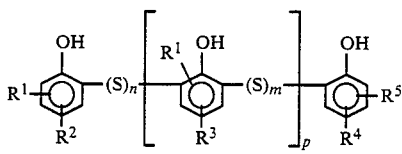

wherein $R^1$, $R^2$, $R^3$, $R^4$ and $R^5$ are hydrogen or the same or different hydrocarbyl groups containing from 1 to 20 carbon atoms, m and n are 1 to 4 and p is 0 to 4 with a boron compound capable of reacting with said hydrocarbyl diol and selected from the group consisting of metaborates, boric acid, and alkylborates of the formula $(R^6O)_xB(OH)_y$ wherein $R^6$ is a $C_1$ to $C_6$ alkyl group, x is 1 to 3 and y is 0 to 2, the sum of x and y being 3, the mole ratio of phenol to diol to boron compound ranging from about 1:1:1 to about 1:6:8, respectively, and at a pressure of about 1 to about 5 atmospheres and a temperature of about 80° C. to about 260° C.

11. The composition of claim 10 wherein R is alkyl, aryl, alkaryl, aralkyl, alkenyl, cycloalkyl or cycloalkenyl.

12. The composition of claim 10 wherein the diol is selected from the group consisting of 1,2-octanediol, 1,2-decanediol, 1,2-dodecanediol, 1,2-tetradecanediol, 1,2-pentadecanediol, 1,2-hexadecanediol, 1,2-heptadecanediol, 1,2-eicosanediol, 1,2-triacontanediol, mixed $C_{15}$ to $C_{18}$ alkanediols, diols derived from the epoxidation of propylene, diols derived from the epoxidation of butylene and mixtures of any of these.

13. The composition of claim 10 wherein $R^1$, $R^2$, $R^3$, $R^4$ and $R^5$ are hydrogen, alkyl, aryl, aralkyl, alkaryl, alkenyl, cycloalkyl or cycloalkenyl groups.

14. The composition of claim 13 wherein the phenol sulfide is a 2,2'-thiobis(alkylphenol) wherein n=2 and p=0, 2,2'-dithiopbis(alkylphenol) wherein n=2 and p=0 and thiobis(alkylphenol) wherein p=1 or 2.

15. The composition of claim 10 wherein the boron compound is boric acid.

16. The composition of claim 10 wherein the alkyl borate is a mono-, di- or trialkyl borate, the alkyl portion being a methyl, ethyl, propyl, butyl, amyl or hexyl group.

17. The composition of claim 10 wherein the diol is a mixture of $C_{15}$ to $C_{18}$ alkanediols, the phenol sulfide is dodecylphenol sulfide and the boron compound is boric acid.

18. The composition of claim 10 wherein the diol is 1,2-hexadecanediol, the phenol sulfide is dodecylphenol sulfide and the boron compound is boric acid.

19. The composition of claim 10 wherein the lubricant is (1) a mineral oil, (2) a synthetic oil or a mixture of synthetic oils, (3) a mixture of (1) and (2) or (4) a grease from (1), (2) or 3.

20. The composition of claim 19 wherein the lubricant is a mineral oil.

21. The composition of claim 19 wherein the lubricant is the synthetic oil of (2).

22. The composition of claim 20 wherein the lubricant is the mixture defined by (3).

23. The composition of claim 19 wherein the lubricant is a grease as defined therein.

24. The composition of claim 23 wherein the grease thickener contains at least 15% by weight of a hydroxyl-containing carboxylate soap thickener.

25. The composition of claim 24 wherein the grease thickener is a calcium-, lithium- or amine-containing hydroxyl carboxylate soap.

26. The composition of claim 10 additionally containing from about 0.01 to 10% by weight of a phosphorus and sulfur compound or a mixture of phosphorus-containing or sulfur-containing compounds to supply an equivalent amount of phosphorus and sulfur.

27. The composition of claim 26 wherein the phosphorus and sulfur compound can be one or more chosen from the group consisting of zinc dithiophosphates, molybdenum dithiophosphates, amine dithiophosphates, ashless dithiophosphates or phosphorodithionyl disulfides.

* * * * *